US005692894A

United States Patent [19]
Schwartz et al.

[11] Patent Number: 5,692,894
[45] Date of Patent: Dec. 2, 1997

[54] THERMOFORMED PLASTIC DENTAL RETAINER AND METHOD OF CONSTRUCTION

[75] Inventors: Dann A. Schwartz; John J. Sheridan, both of Metairie, La.

[73] Assignee: Raintree Essix, Inc., New Orleans, La.

[21] Appl. No.: 630,970

[22] Filed: Apr. 8, 1996

[51] Int. Cl.$^6$ .................................................. A61C 3/00
[52] U.S. Cl. .................................................... 433/6
[58] Field of Search ........................................ 433/6

[56] References Cited

U.S. PATENT DOCUMENTS

| 3,950,851 | 4/1976 | Bergersen | 433/6 |
| 4,055,895 | 11/1977 | Huge | 433/6 |
| 5,536,168 | 7/1996 | Bourke | 433/6 |
| 5,624,257 | 4/1997 | Farrell | 433/6 |

*Primary Examiner*—John J. Wilson
*Attorney, Agent, or Firm*—John M. Harrison

[57] ABSTRACT

A thermoformed plastic dental retainer and method of selectively straightening crooked or maloccluded teeth and retaining the straightened teeth using the retainer. The dental retainer is constructed by first forming an impression of a patient's upper or lower dentition and constructing a cast from the impression. The retainer is vacuum thermoformed over the cast using a sheet, plate or disc of thermoformable plastic and a vacuum or pressure thermoforming machine. A protrusion or divot is formed in the retainer on the labial or lingual side of each tooth which is to be repositioned lingually or labially, respectively, and a gap, opening or window is formed in the retainer on the opposite side of the divot to accommodate unhindered tooth repositioning movement. As the retainer is worn on the patient's dentition over a period of days or weeks, the projecting divots apply pressure to the respective teeth and push the teeth into the gap or window of the retainer to a straightened position. By appropriately positioning the divots in the retainer with respect to the patient's malpositioned teeth, the teeth may be moved libially, lingually or rotated, as needed, for straightening.

18 Claims, 2 Drawing Sheets

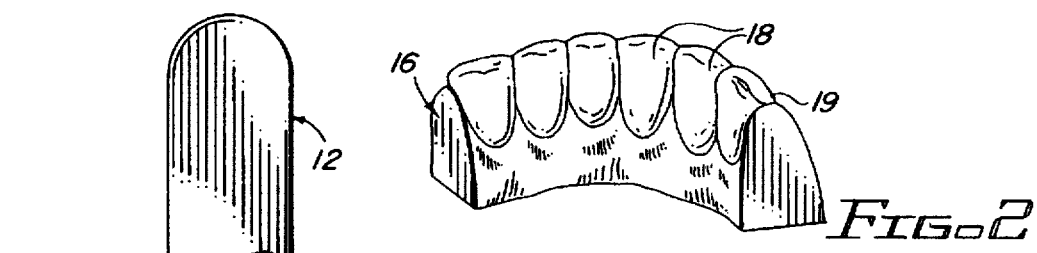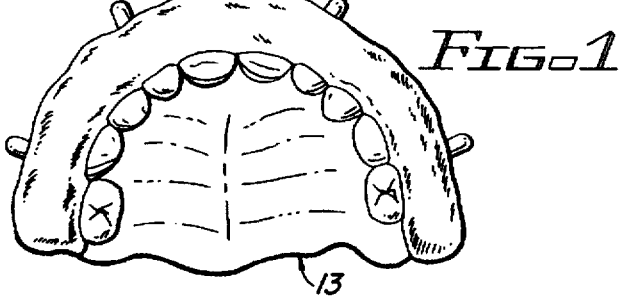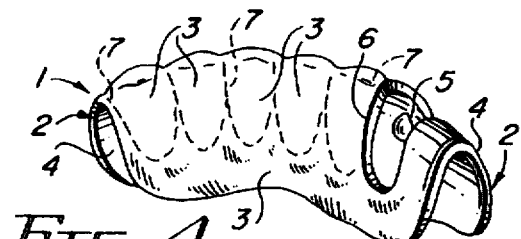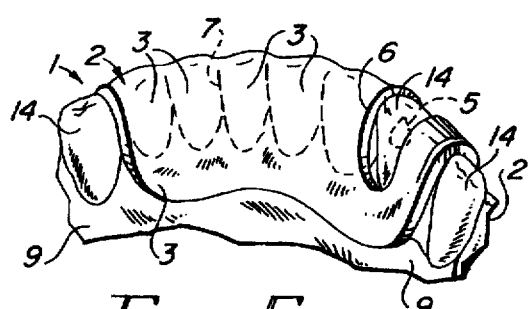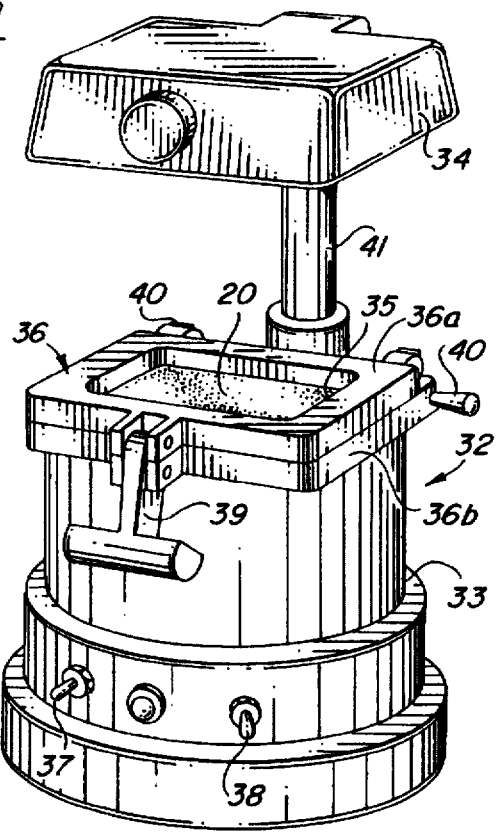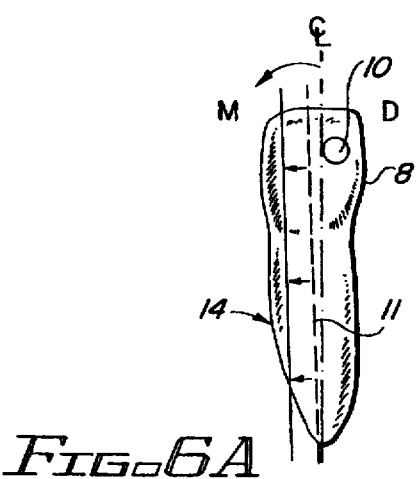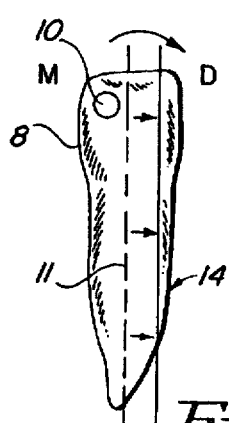

THERMOFORMED PLASTIC DENTAL RETAINER AND METHOD OF CONSTRUCTION

BACKGROUND OF THE INVENTION

Field of the Invention

This invention relates to dental retainers or appliances for straightening and retaining teeth and more particularly, to a thermoformed plastic dental retainer and method of straightening a selected crooked or malpositioned tooth or teeth of a patient's upper or lower anterior dentition using the retainer. In a preferred embodiment the thermoformed plastic dental retainer is constructed from a sheet, plate or disc of thermoformable plastic. An impression of the patient's dentition is first made using a suitable impression material such as polyvinyl siloxane. A cast is then constructed from the impression and the retainer is heat-formed in the thermoplastic sheet on the cast using a vacuum or pressure thermoforming machine. A protrusion or divot is formed in the retainer and a gap, opening or window on the opposite side of each tooth which needs repositioning. The divot is formed to induce force for tooth movement and the window is cut into the appliance to allow the tooth to be repositioned. The divot can be incrementally deepened at subsequent patient's visits to generate additional movement, as hereinafter described. As the retainer is worn on the dentition over a period of weeks, the projecting divots apply repositioning pressure to the teeth and the teeth are slowly moved to their straightened positions into the windows, which allows unhindered movement of the slowly repositioning teeth. By appropriately positioning the divot and window in the impression of the retainer formed by a given crooked or maloccluded tooth, the tooth can be repositioned labially, lingually or by rotation, as needed, to achieve a more esthetically-pleasing dentition.

The thermoformable plastic dental retainer of this invention represents a considerable improvement over conventional teeth straightening and retaining devices in several respects. The retainer can be used to retain the dentition of finished orthodontic cases at a fraction of the cost and with fewer problems than conventional devices. Unlike conventional wire braces, the clear retainer is esthetically-pleasing to the patient and usually requires no periodic adjustment, affording the clinician significant relief in chair time and administrative detail.

It is therefore an object of this invention to provide a new and improved dental appliance for straightening and retaining crooked or maloccluded teeth.

Another object of this invention is to provide a thermoformed plastic dental retainer for straightening and retaining malpositioned teeth, which retainer has an esthetically-pleasing appearance when worn by the patient.

Still another object of this invention is to provide a thermoformed plastic dental retainer having a series of oppositely-positioned protruding divots and windows for selectively repositioning crooked, maloccluded or twisted teeth, wherein the divots apply pressure to the teeth in the direction of repositioning and the windows provide space for unhindered repositioning movement of the teeth, as the retainer is worn on the dentition over a selected period of time.

Yet another object of this invention is to provide a method of straightening the malpositioned teeth of a patient's dentition and retaining the straightened teeth, including the steps of creating an impression of the patient's dentition, constructing a cast from the impression, heat-forming a dental retainer on the cast using a sheet of thermoformable plastic and constructing one or more divots and windows in the retainer on the labial or lingual side, as appropriate, of teeth which are to be repositioned, and wearing the retainer on the patient's dentition for a selected period of time, wherein the divots apply pressure to the respective teeth in the direction of repositioning and the oppositely-positioned windows provide repositioning space for the teeth.

SUMMARY OF THE INVENTION

These and other objects of the invention are provided in a transparent thermoformed plastic dental retainer and method of straightening malpositioned teeth using the retainer, which retainer is worn on a dental patient's upper or lower anterior dentition for repositioning or straightening crooked or maloccluded teeth to a straightened, esthetically-pleasing configuration. In a preferred embodiment the retainer is constructed by first forming an impression of the patient's upper or lower anterior dentition using a suitable impression material, constructing a cast of the patient's dentition from the impression and forming the retainer on the cast by heating and vacuum or pressure-sealing a sheet of thermoformable plastic over the dentition of the cast. A divot is selectively formed in the retainer on the labial or lingual side of the tooth or teeth which are to be repositioned, and a window is cut in the retainer on the opposite side of the divot to provide repositioning space for the tooth or teeth. As the retainer is worn on the teeth over a selected period of time, the divots apply pressure to the malpositioned teeth in the direction of repositioning. Depending upon the location of the divots in the retainer, a variety of biomechanical forces can be exerted on the teeth in order to achieve a host of straightening and repositioning effects.

BRIEF DESCRIPTION OF THE DRAWINGS

The invention will be better understood by reference to the accompanying drawings, wherein:

FIG. 1 is a top view of a patient's dental impression, formed in a standard or conventional dental impression tray;

FIG. 2 is a perspective view of a dental impression cast formed from a dental impression, taken from the upper or lower anterior dentition of a patient;

FIG. 3 is a perspective view of a standard or conventional vacuum thermoforming machine used in forming the thermoformed plastic dental retainer of this invention;

FIG. 4 is a rear view of a preferred embodiment of the thermoformed plastic dental retainer, more particularly illustrating a typical divot and window location with respect to a tooth to be straightened;

FIG. 5 is a rear view of the thermoformed plastic dental retainer, more particularly illustrating the retainer engaging a patient's lower anterior dentition, with a divot and window combination in place;

FIG. 6A is a front view of a tooth of a lower anterior dentition, illustrating repositioning of the tooth by distal rotation thereof using the thermoformed plastic dental retainer;

FIG. 6B is a front view of a tooth of the lower anterior dentition, illustrating repositioning of the tooth by distal rotation thereof;

DESCRIPTION OF THE PREFERRED EMBODIMENTS

Figure 8:
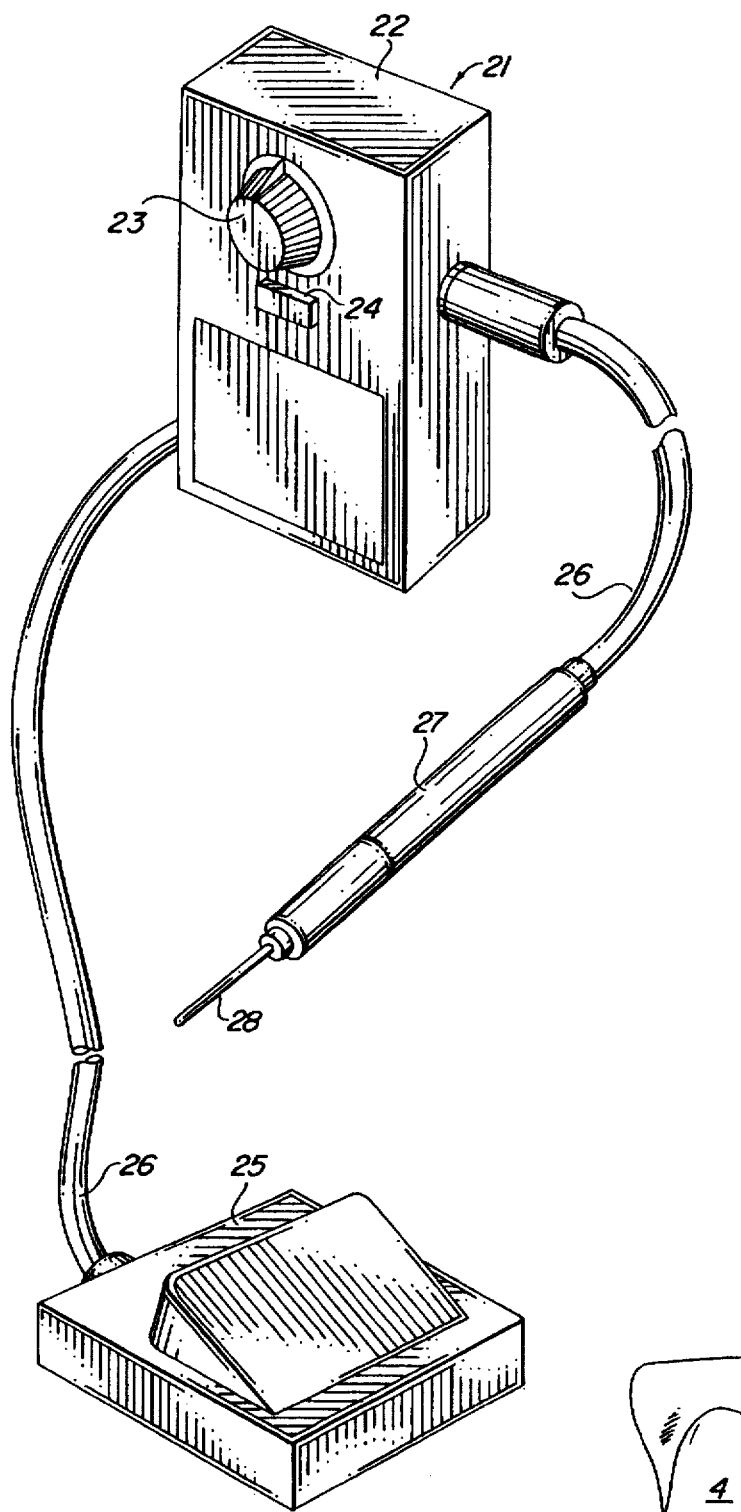
FIG. 8 is a perspective view of a typical heating probe device used in forming divots in the thermoformable plastic dental retainer.

Referring initially to FIGS. 1–5 of the drawings, the thermoformed plastic dental retainer, hereinafter referred to as the retainer, of this invention is generally illustrated by reference numeral 1. The retainer 1 is characterized by a retainer body 2, vacuum-formed from a sheet of thermoformable plastic material (not illustrated) on a dental cast 16, illustrated in FIG. 2. The dental impression cast 16 is formed from a conventional dental impression tray 12 shown in FIG. 1, using a pressure machine (not illustrated) or a conventional vacuum thermoforming machine 32 (illustrated in FIG. 3), as hereinafter further described. The retainer body 2 is characterized by multiple tooth impressions 7, corresponding to the respective teeth of the patient's lower anterior dentition and illustrated in phantom in FIGS. 4 and 5. The retainer body 2 includes a lingual surface 3, which, during retainer use, covers the lingual gingiva 9 of the dentition and a facial or labial surface 4, which covers the labial surface (not illustrated) of the dentition. Projecting divots 5 are formed in the labial or lingual surface of the retainer body 2 and extend into the plastic tooth impressions 7 corresponding to teeth which are in need of repositioning, as hereinafter further described. Openings or windows 6 are cut in the retainer body 2 on the opposite labial or lingual side from the respective divots 5, to accommodate repositioning movement of the teeth in the tooth socket (not illustrated), as the divots 5 apply constant repositioning pressure to the respective teeth 14 while the retainer 1 is worn on the dentition over a period of time, as illustrated in FIG. 5. The retainer body 2 is maintained in position on the patient's dentition by snugly engaging or "snapping into" the natural undercuts below the contact points of adjacent teeth, and may be removed as desired.

Referring now to FIGS. 1–3 of the drawings, the retainer 1 is constructed by first making a dental impression 13 of the patient's upper or lower dentition, or both, using a suitable impression material such as polyvinyl siloxane and a standard or conventional dental impression tray 12, illustrated in FIG. 1. A dental cast 16 is then made from that portion of the dental impression 13 corresponding to the area of malposed teeth, usually the anterior dentition, or that portion of the dentition extending from the left canine to the right canine, as illustrated in FIG. 2. The dental cast 16 includes a lingual surface 17, a labial surface (not illustrated) and cast teeth 18. Preparatory to forming the retainer 1, the dental cast 16 is trimmed such that the occlusal surfaces 19 of the cast teeth 18 have a slanted or tapered configuration, as further illustrated in FIG. 2, to facilitate easy removal of the retainer body 2 from the dental cast 16. Because the retainer 1 is maintained in position on the patient's dentition by "snapping into" the multiple undercuts below the contact points of adjacent teeth, the undercuts on the dental cast 16 may need trimming for augmentation if their presence on the cast is not evident. As illustrated in FIG. 3, a standard or conventional pressure machine or a vacuum thermoforming machine 32, having a base 33 with a perforated top vacuum plate 35 and a heating unit 34 extending from the base 33 and mounted on a frame post 41 and energized by a heater switch 37, is used to vacuum thermoform a retainer body 2 having tooth impressions 7 matching the cast teeth 18 of the dental cast 16. The vacuum thermoforming machine 32 also includes a slidable frame 36 having a top frame member 36a hinged to a bottom frame member 36b. The top frame member 36a is removably latched to the bottom frame member 36b by means of a frame latch knob 39. A vacuum motor (not illustrated) is contained in the base 33 and energized by a vacuum motor switch 38. Alternatively, a conventional pressure thermoforming machine (not illustrated) can be used to shape the retainer body 2 over the cast 16 according to the knowledge of those skilled in the art.

The retainer body 2 is formed on the dental cast 16 by first energizing the heating unit 34 of the vacuum thermoforming machine 32 by means of the heater switch 37. The dental cast 16 is then placed on the perforated vacuum plate 35 of the base 33, with the cast teeth 18 of the dental cast 16 facing upwardly. Before the frame 36 is raised on the frame post 41 by means of frame lift knobs 40 to within a suitable heating distance of the heating unit 34, the top frame member 36a is pivoted upwardly with respect to the bottom frame member 36b and a thermoformable plastic plate 20 is centered on the bottom frame member 36b. The top frame member 36a is then pivoted downwardly and secured by means of the frame latch knob 39, and the frame 36 is raised on the frame post 41 such that the thermoformable plastic plate 20 is located immediately beneath the heating unit 34. After approximately 25 to 50 seconds, the thermoformable plastic plate 20 is heated to a suitable thermoforming temperature and begins to sag slightly. The vacuum motor in the base 33 is then energized by means of the vacuum motor switch 38 and the frame 36 is rapidly lowered on the frame post 41 over the vacuum plate 35 by means of the frame lift knobs 40, such that the softened thermoformable plastic plate 20 is first draped and then tightly vacuum-pulled over the dental impression cast 16. After ten to fifteen seconds, the retainer body 2 has been formed from the thermoformable plastic plate 20 positioned over the dental cast 16 and the heating unit 34 is turned off. The molded retainer body 2 is then removed from the dental cast 16 after the retainer body 2 has cooled to room temperature.

Figure 9:
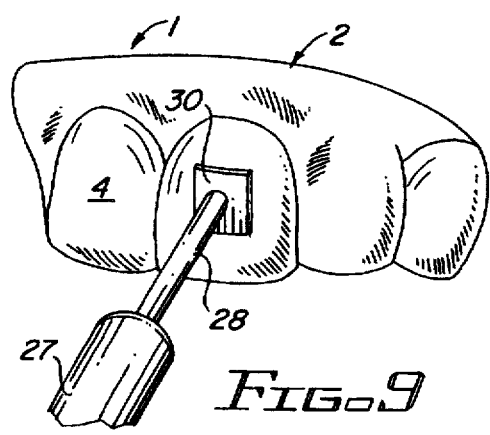
FIG. 9 is a perspective view, partially in section, of a thermoformed plastic dental retainer, more particularly illustrating a preferred technique for reinforcing a divot formed in the retainer.

Referring again to FIGS. 4, 5, 8 and 9 of the drawings, after the plastic retainer body 2 is removed from the dental cast 16, the plastic tooth impressions 7 which correspond to the teeth of the patient's dentition needing straightening or repositioning, are configured in the retainer body 2. For teeth in need of lingual repositioning, divots 5 are formed as hereinafter described in the labial surface 4 of the retainer body 2 and extend into the respective plastic tooth impressions 7, as illustrated in FIGS. 4 and 5. Windows 6 are then cut or burred in the lingual surface 3 of the plastic tooth impressions 7 in the plastic retainer body 2, thus opening the respective plastic tooth impressions 7 opposite the divots 5, as further illustrated in FIGS. 4 and 5. For teeth requiring labial repositioning, divots 5 are formed in the lingual surface 3 of the retainer body 2 and extend into the respective plastic tooth impressions 7, opposite to the divot 5 configuration illustrated in FIGS. 4 and 5. In like manner, windows 6 are cut in the opposite, labial surface 4, thus opening the respective plastic tooth impressions 7 in the labial surface 4, opposite the window 6 illustrated in FIGS. 4 and 5. As illustrated in FIG. 8, a typical divot-forming device 21 includes a control module 22 having a rheostat 23 and a manual power switch 24. A handle 27 having a heating probe 28 protruding from the end thereof, is wired to the control module 22 by means of wiring 26. A foot power switch 25 is also wired to the control module 22 by means of wiring 26. The divot 5 is made in the retainer body 2 by adjusting the heating probe 28 to a suitable temperature which will shape and form, rather than melt, the plastic. (This temperature is typically achieved by setting the rheostat 23 to the 12 o'clock position). The heating probe 28 is then dipped in a high temperature oil, which prevents distortion and imploding of the divot when the metal healing probe 28 is removed from the plastic. The initial divot 5 is approximately 1mm deep and can be further deepened at subsequent appointments, as hereinafter described, depending on the required tooth repositioning distance. Each corresponding window 6 provides the space for the repositioning tooth to move to a straightened position as the retainer 1 is worn on the upper or lower anterior dentition over a period of time. As illustrated in FIG. 9, the divot 5 may be periodically reinforced and deepened by lining the divot 5 with additional thermoformable plastic. To implement this procedure, a divot reinforcing plastic patch 30 is first cut from a sheet of thermoformable plastic. The heating probe 28 of the divot forming device 21 is dipped in the oil and the plastic patch 30 placed on the end of the heating probe 28. The plastic patch 30 is then pressed into the existing divot 5 to be deepened by means of the heating probe 28 and caused to thermoseal with the retainer body 2. Reinforcing the divot 5 in this manner may be necessary for repeated or periodic enlargement, deepening or other adjustment of the divot 5 during the tooth repositioning period, especially under circumstances where the tooth is to be extensively moved.

Figure 7:
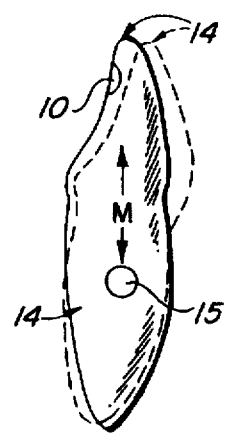
FIG. 7 is a lateral view of a tooth of the lower anterior dentition, illustrating repositioning of the tooth by tipping the crown of the tooth forwardly.

Referring now to FIGS. 5–7, the respective divots 5 can be used to apply a variety of biomechanical forces on the malpositioned tooth or teeth of a dentition, depending on the position of each divot 5 in the retainer body 2. As illustrated in FIGS. 5 and 6A, if the contact point 10 of the divot 5 is located distally on the crown 8 of a tooth 14, the tooth 14 will tend to be rotated in a mesial direction about the vertical axis of rotation 11 of the tooth 14, as illustrated by the arrow; conversely, if the divot contact point 10 is applied mesially to the crown 8 of the tooth 14, as illustrated in FIG. 6B, the tooth 14 will be rotated in a distal direction about the vertical axis of rotation 11, as illustrated by the arrow. Accordingly, distal or mesial positioning of the divot 5 in the retainer body 2 is especially useful in straightening twisted teeth. Furthermore, as illustrated in FIG. 7, positioning of a divot contact point 10 incisally on the tooth 14 will tend to tip the crown 8 of the tooth 14 to a rearward position about the horizontal axis of rotation 15 of the tooth 14.

It will be appreciated by those skilled in the art that the retainer 1 of this invention may be used to straighten and/or retain teeth with much more patient comfort, both physically, emotionally, as the clear plastic is not an esthetic concern, than is possible using conventional wire braces.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A removable thermoformed plastic dental retainer for wearing on a dentition and straightening malpositioned teeth, comprising a plastic retainer body having a plurality of tooth impressions for receiving respective teeth of the dentition, each of said tooth impressions having a labial surface on one side thereof and a lingual surface on the opposite side thereof; at least one divot formed in at least one of said labial surface and said lingual surface, said divot extending into a corresponding one of said tooth impressions for exerting respositioning pressure on at least one of the teeth of the dentition, and at least one window shaped in at least one of said labial surface and said lingual surface opposite said at least one divot, said window opening said corresponding one of said tooth impressions for accommodating repositioning movement of the respective teeth of the dentition, responsive to placement of said retainer on the dentition of the patient for a selected period of time.

2. The retainer of claim 1 wherein said tooth impressions comprise impressions of at least the canine, lateral incisor and central incisor teeth of the dentition.

3. The retainer of claim 1 wherein said at least one divot comprises two divots selectively formed in said labial surface and said lingual surface, respectively, of said tooth impressions, said divots extending into said tooth impressions, respectively, for exerting repositioning pressure on respective teeth of the dentition when the retainer is seated on the dentition and said at least one window comprises two windows selectively shaped in said labial surface and said lingual surface, respectively, of said tooth impressions, said windows opening said tooth impressions, respectively, for accommodating repositioning movement of the respective teeth of the dentition.

4. The retainer of claim 3 wherein said tooth impressions comprise tooth impressions of at least the canine, lateral incisor and central incisor teeth of the dentition.

5. The retainer of claim 1 wherein said divot is formed distally in said labial surface of said plastic retainer body for repositioning the respective teeth of the dentition in a mesial direction.

6. The retainer of claim 1 wherein said divot is formed medially in said labial surface of said plastic retainer body for repositioning the respective teeth of the dentition in a distal direction.

7. The retainer of claim 1 wherein said divot is formed in said labial surface of said plastic retainer body for tipping the respective teeth of the dentition in a lingual direction.

8. The retainer of claim 1 wherein said divot is formed in said lingual surface of said plastic retainer body for tipping the respective teeth of the dentition in a labial direction.

9. The retainer of claim 1 wherein said divot is formed in said labial surface of said plastic retainer body for displacing the respective teeth of the dentition in a lingual direction.

10. The retainer of claim 1 wherein said divot is formed in said lingual surface of said plastic retainer body for displacing the respective teeth of the dentition in a labial direction.

11. A method of straightening malpositioned teeth of a patient's upper dentition, comprising the steps of constructing a dental impression cast of the upper dentition; forming from said dental impression cast a retainer body having a plurality of tooth impressions for receiving respective teeth of the upper dentition, each of said tooth impressions having a labial surface on one side thereof and a lingual surface on the opposite side thereof; forming at least one divot in at least one of said labial surface and said lingual surface for extending into a corresponding one of said tooth impressions and exerting repositioning pressure on a corresponding one of the teeth of the upper dentition; shaping at least one window in at least one of said labial surface and said lingual surface opposite said divot, said window opening said tooth impressions for accommodating repositioning movement of the corresponding teeth of the upper dentition; and wearing said retainer body on the upper dentition for a selected period of time to straighten the malpositioned teeth.

12. The method of claim 11 comprising the step of forming an impression of the patient's upper dentition and wherein said dental impression cast is constructed from said impression.

13. The method of claim 11 wherein said tooth impressions comprise tooth impressions of the canine, lateral incisor and central incisor teeth of the upper dentition.

14. The method of claim 11 comprising the step of forming an impression of the patient's upper dentition and wherein said dental impression cast is constructed from said impression and said tooth impressions comprise tooth impressions of the canine, lateral incisor and central incisor teeth of the upper dentition.

15. A method of straightening malpositioned teeth of a patient's lower dentition, comprising the steps of constructing a dental impression cast of the lower dentition; forming from said dental impression cast a retainer body having a plurality of tooth impressions for receiving respective teeth of the lower dentition, each of said tooth impressions having a labial surface on one side thereof and a lingual surface on the opposite side thereof; forming at least one divot in at least one of said labial surface and said lingual surface for extending into a corresponding one of said tooth impressions and exerting repositioning pressure on a corresponding one of the teeth of the lower dentition; shaping at least one window in at least one of said labial surface and said lingual surface, opposite said divot, said window opening said tooth impressions for accommodating repositioning movement of the corresponding teeth of the lower dentition; and wearing said retainer body on the lower dentition for a selected period of time to straighten the malpositioned teeth.

16. The method of claim 15 comprising the step of forming an impression of the patient's lower dentition and wherein said dental impression cast is constructed from said impression.

17. The method of claim 15 wherein said tooth impressions comprise tooth impressions of the canine, lateral incisor and central incisor teeth of the lower dentition.

18. The method of claim 15 comprising the step of forming an impression of the patient's lower dentition and wherein said dental impression cast is constructed from said impression and said tooth impressions comprise impressions of the canine, lateral incisor and central incisor teeth of the lower dentition.

* * * * *